(12) United States Patent
Muller et al.

(10) Patent No.: US 6,493,884 B1
(45) Date of Patent: Dec. 17, 2002

(54) METHOD AND DEVICE FOR COLLECTING URINE

(76) Inventors: Peter H. Muller, 135 Charles St., Los Gatos, CA (US) 95032; David Shear, 1431 Floribunda Ave., #1, Burlingame, CA (US) 94010; Mary Shear, 12247 Laurel Terr. Dr., Studio City, CA (US) 91604

( * ) Notice: Subject to any disclaimer, the term of this patent is extended or adjusted under 35 U.S.C. 154(b) by 0 days.

(21) Appl. No.: 09/909,741

(22) Filed: Jul. 19, 2001

(51) Int. Cl.[7] ............................................. A47K 11/00
(52) U.S. Cl. ........................ 4/144.2; 141/337; 141/338
(58) Field of Search ........................ 4/144.1–144.4; 141/337, 338

(56) References Cited

U.S. PATENT DOCUMENTS

| | | | |
|---|---|---|---|
| 987,360 A | 3/1911 | Harrington | |
| 1,256,961 A | 2/1918 | Welsh | |
| 1,408,865 A | 3/1922 | Cowell | |
| 1,503,737 A | 7/1924 | Parker | |
| 1,563,005 A | 11/1925 | Allee | |
| 2,685,399 A | 8/1954 | Crosby | 229/22 |
| 2,734,198 A | 2/1956 | Kutsche | 4/110 |
| D178,749 S | 9/1956 | Bachechi | 83/1 |
| 2,796,864 A | 6/1957 | Johnson | 128/294 |
| 2,878,486 A | 3/1959 | Bartlett et al. | 4/110 |
| 3,099,017 A | 7/1963 | Sullivan | 4/110 |
| D195,930 S | 8/1963 | Hill | D83/1 |
| 3,172,130 A | 3/1965 | Lange | 4/110 |
| 3,177,500 A | 4/1965 | Bauman | 4/110 |
| D208,609 S | 9/1967 | Garland | D83/1 |
| 3,346,883 A | 10/1967 | Ersek | 4/1 |
| 3,572,318 A | 3/1971 | Garland | 128/2 |
| 3,579,652 A | 5/1971 | Ericson | 4/110 |
| 3,625,654 A | 12/1971 | Van Duyne | 23/253 |
| D227,413 S | 6/1973 | Sherin | D83/1 |
| 3,811,136 A | 5/1974 | Whitney et al. | 4/110 |
| 4,176,412 A | 12/1979 | Peterson | 4/144.1 |
| 4,286,634 A | 9/1981 | Wisner | 141/95 |
| 4,296,502 A * | 10/1981 | Bortle | 4/144.1 |
| 4,559,649 A | 12/1985 | Burnett | 4/144.1 |
| 4,681,573 A | 7/1987 | McGovern et al. | 604/329 |
| 4,696,067 A | 9/1987 | Woodward | 4/144.1 |
| D302,042 S | 7/1989 | McGovern et al. | D24/54 |
| D303,572 S | 9/1989 | Parrish | D24/54 |
| 5,078,189 A | 1/1992 | Ronsonet | 141/337 |
| 5,235,705 A * | 8/1993 | Belisle | 4/144.3 |
| D340,768 S | 10/1993 | Jabour | D24/122 |
| 5,330,453 A | 7/1994 | Cornellier | 604/329 |
| 5,401,263 A | 3/1995 | Cornellier | 604/329 |
| 5,409,315 A | 4/1995 | Evans | 383/1 |
| D374,281 S | 10/1996 | Markles | D24/122 |
| 5,602,161 A | 2/1997 | Cross | 128/771 |
| 5,857,504 A | 1/1999 | Tremblay | 141/338 |
| D406,644 S | 3/1999 | Keppler | D23/302 |
| 5,920,916 A | 7/1999 | Norton | 4/144.3 |
| 6,116,780 A * | 9/2000 | Young et al. | 4/144.2 X |
| 6,152,198 A * | 11/2000 | Nguyen | 141/337 |

* cited by examiner

*Primary Examiner*—Charles E. Phillips
(74) *Attorney, Agent, or Firm*—Michael A. Glenn

(57) ABSTRACT

A method and apparatus are disclosed for collecting urine samples. The method and apparatus comprise a reservoir and funnel. The bottom portion of the funnel is attached to the top portion of the reservoir. The funnel has ridges lying along the long axis of the funnel. The funnel has an expanded and unexpanded position. When unexpanded the funnel folds inward along the ridge about the lip of the reservoir, towards the bottom of the reservoir. When expanded, the funnel folds upwardly and unfolds outwardly.

31 Claims, 3 Drawing Sheets

METHOD AND DEVICE FOR COLLECTING URINE

BACKGROUND OF THE INVENTION

1. Technical Field

The invention relates to funnels, and more particularly to collapsible urine sample collection methods and devices.

2. Description of the Prior Art

The collection of urine specimens for urinalysis requires a patient, or other subject, to urinate into a reservoir-like container while standing or sitting. The container is either disposable or reusable and may or may not have an associated lid. This procedure can prove awkward, messy, and unsanitary. Improper sterilization of a reusable container by a laboratory can result in the transmission of infectious or virulent particles onto a user's skin and genitalia.

Attempts to improve the efficiency and sanitation of this procedure have fallen generally into two categories; the development of various funnel-shaped devices and the development of funnel or tube-shaped devices associated with a container. Examples of funnel-shaped devices are disclosed in Packer, Urine conducting apparatus, U.S. Pat. No. 3,964,111, (Jun. 22, 1976), and in U.S. Pat. Nos. Des. 158,693; Des. 178,749; Des. 195,930; Des. 208,609; and Des. 249,997.

Examples of funnel-shaped devices in conjunction with urine specimen containers are disclosed in Gibson, Urine Collection Shield, U.S. Pat. No. 3,171,136, Jun. 6, 1960; Friedman et al, Female Urinal, U.S. Pat. No. 3,473,172, (Aug. 5, 1965); Van Duyne, Urine Collection Device, U.S. Pat. No. 3,625,654, (May 22, 1970); Leiser, Portable Urinal, U.S. Pat. No. , 3,703,731, (Nov. 28, 1972); and in U.S. Pat. Nos. Des. 138,651; Des. 212,792; and Des. 227,413.

FIGS. 1A and 1B are perspective views of an example of a conventional collapsible funnel. A collapsible funnel is disclosed in Klebold, Combination collapsible funnel and canister therefor, U.S. Pat. No. 4,557,378, (Dec. 10, 1985).

FIG. 1A illustrates the funnel 10 in its collapsed form. The funnel 10 is comprised of a plurality of nested rings terminating in an outer ring 12. As can be seen in FIG. 1B, when the inner ring 14 is pulled away from the outer ring 12, a series of telescoping segments 16 extend to form the extended funnel 10. The inner ring 14 is inserted within the opening in a reservoir to be filled, and the fluid is poured into the opening 18 in the funnel 10.

Nguyen, Retractable funnel, U.S. Pat. No. 6,152,198, (Nov. 28, 2000) discloses a retractable funnel that comprises a base which is insertable within an existing reservoir, and that has a plurality of fins extending outwardly from the base. The fins are configured so that they collapse to form a tube, such that the funnel can be slid into the reservoir. Each of the tips of the fins includes lip segments provided to form a continuous lip ring when the fins are collapsed into the tube. The preferred lip ring prevents the funnel from falling into the reservoir, while still permitting the lid of the reservoir to be attached over the funnel. The funnel's base further includes a ridge running around its periphery to restrain the funnel from being inadvertently removed from the reservoir when extending the funnel for use.

One problem with prior art funnels is that they take an appreciable amount of time to implement, they are difficult to use, and often collapse on accident. This can result in a user depositing their specimen onto the floor rather than into the reservoir. What is needed is a retractable funnel that can be implemented quickly and one that will easily stay in place once implemented. What is needed is a funnel and reservoir system that allows for the easy insertion of a pipet.

SUMMARY OF THE INVENTION

A method and apparatus is disclosed for collecting urine samples. The method and apparatus comprises a reservoir and funnel. The bottom portion of the funnel is attached to the top portion of the reservoir. The funnel has ridges lying along its long axis. The funnel has an expanded and unexpanded position. When unexpanded the funnel folds inward along the ridges and rotates inward about the lip of the reservoir, towards the bottom of the reservoir. When expanded, the funnel rotates upward and unfolds outward.

The mouth of the funnel has a circular or contoured shape. The contoured shape is saddle shaped so that the funnel mouth follows the natural contours of the perineum allowing the funnel to be placed closely to the subject's body.

DESCRIPTION OF THE PREFERRED EMBODIMENT

Figure 1A:
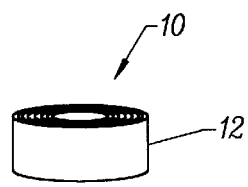
FIGS. 1A and 1B are perspective views of a conventional collapsible funnel.
Figure 1B:
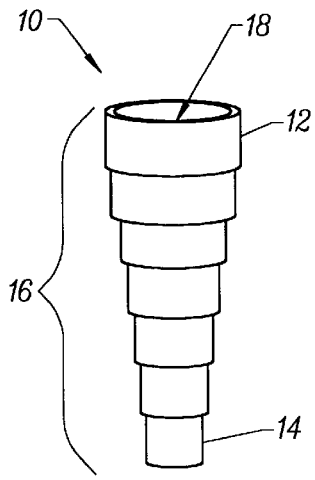
Figure 3:
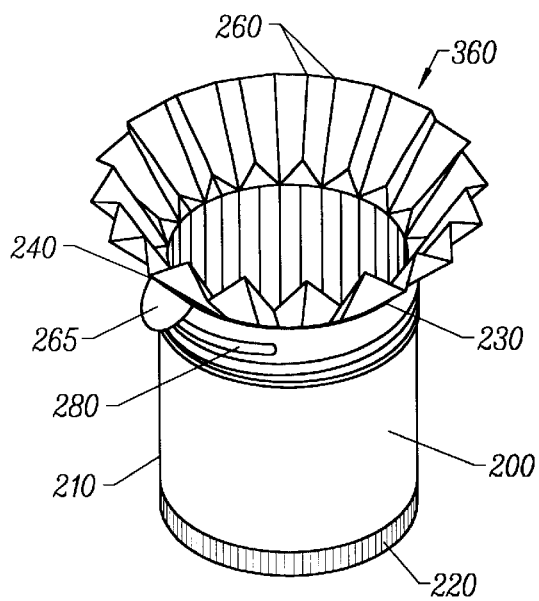
FIG. 3 is a diagram illustrating a urine specimen collection system in an expanded position according to the invention.
Figure 2:
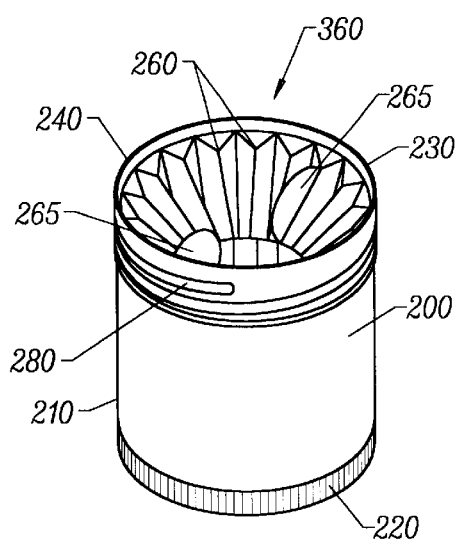
FIG. 2 is a diagram illustrating a urine specimen collection system in an unexpanded position according to the invention.

Referring to FIGS. 2 and 3, the specimen reservoir 200 of the invention has a reservoir wall 210 that encloses a reservoir interior of uniform cross-sectional diameter from the reservoir base 220 to the joint of reservoir wall 210 with a cylindrical mouth segment 230. A urine specimen is collected into this reservoir and then stored for future urinalysis.

Here, as elsewhere in these descriptions, vertical dimensions (top, base, upward, downward) refer to a static model of the invention in its storage orientation and are not meant to limit the functionality of the invention in its collection state. Centrical dimensions (inner, inward, outer, outward) refer to the axis of symmetry of the specimen reservoir 200 as central.

The connecting portion of the funnel 240 lies flush against the inner face of the specimen reservoir 200 providing a high degree of axial stability for the funnel in relation to the specimen reservoir 200. The funnel 360 has ridges 260 along its long axis. The funnel folds along these ridges.

In FIG. 2, the funnel 360 is in an unexpanded position. In an unexpanded position the ridges 260 lie closely together. The funnel is integrated with the specimen reservoir or is inserted into the reservoir.

In FIG. 3, the ridges 260 lie farther apart when expanded. While Applicant has disclosed a funnel which folds along its long axis herein, it will be appreciated by those skilled in the art that such a funnel readily encompasses any device or step, that can be substituted therefore to effect a similar result as is achieved by the ridges, including but not limited to ridges along the short axis of the funnel.

The funnel 360 is foldable inwardly and outwardly between the unexpanded and expanded positions, respectively. While in an unexpanded position the funnel 360 lies substantially within the reservoir 200, providing for a compact package. While expanded, the funnel 360 lies substantially outside the reservoir 200, forming a wide mouth. A wide mouth provides for easy urine collection.

A tab extension 265 is connected to the funnel for moving the funnel between the unexpanded and expanded positions. A user holds the tab 265 while pushing or pulling on the funnel, causing the funnel to rotate. In a preferred embodiment, two tab extensions 265 are attached on opposite sides on the outer surface of the funnel. The placement of the tabs provides an easy way to move the funnel inwardly and outwardly while reducing the possibility that the urine specimen will come into contact with the user, because the user is shielded from the urine specimen by the funnel walls.

The parallel sides of the funnel mouth allow it to be held easily between the user's legs during collection of a specimen. Typically the shape of the funnel mouth is circular.

Figure 4:
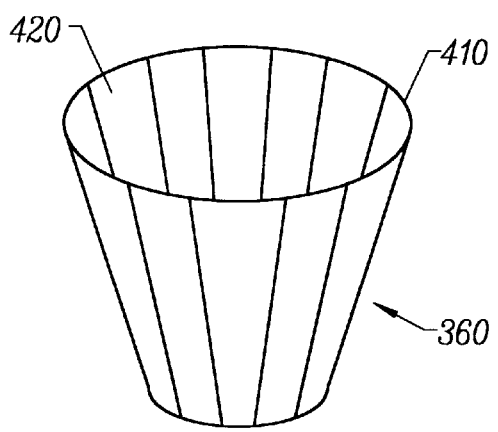
FIG. 4 is a diagram illustrating a saddle-shaped funnel according to the invention.

FIG. 4 illustrates another preferred embodiment where the funnel mouth of the funnel 360 is saddle shaped. The saddle-shaped mouth features a narrow 410 and wide portion 420. This configuration is especially accommodating for specimen collection where a subject has poor directional control.

After the specimen has been collected a lid is screwed onto the reservoir, using the grooves 280 located on the outside of the reservoir. Alternatively, a pipet can be inserted through the space formed by the funnel, without having to fold the funnel, to remove the specimen from the reservoir.

The reservoir 200 and funnel 360 is preferably to be molded of an inexpensive, generally rigid plastic material that has sufficient resiliency to enable the engagement and disengagement of the various parts. Other materials such as metals, rubbers and paper are also contemplated.

Figure 5:
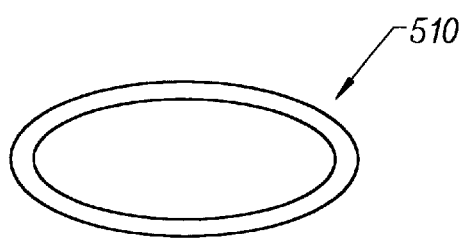
FIG. 5 is a diagram illustrating a liner according to the invention.

FIG. 5 illustrates a preferred embodiment of a liner 510 used to adaptably secure the funnel 360 to the reservoir 200. The liner 510 is cylindrical in shape and lies between the connecting portion of the funnel and the reservoir. The liner 510 resists leaks that may occur between the connecting portion of the funnel and the reservoir. The liner 510 also can be integrated with either the funnel or the reservoir.

Figure 6:
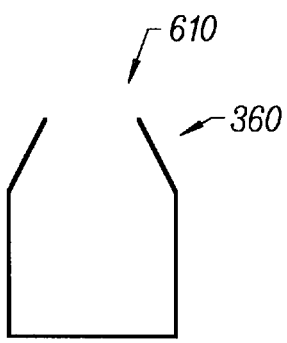
FIG. 6 is a diagram illustrating a funnel folded in a position to form a spout according to the invention.

FIG. 6 illustrates another embodiment where the funnel 360 is folded to a position such that it forms a spout 610. The spout 610 allows the easy pouring of the urine sample into other enclosures such as a test tube.

Figure 7A:
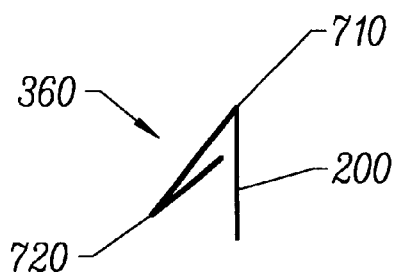
FIGS. 7A, 7B and 7C are diagrams illustrating the funnel folding about itself when moving between an expanded and unexpanded position according to the invention.
Figure 7B:
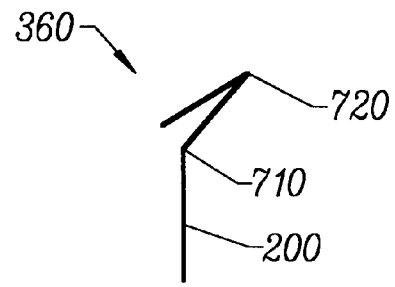
Figure 7C:
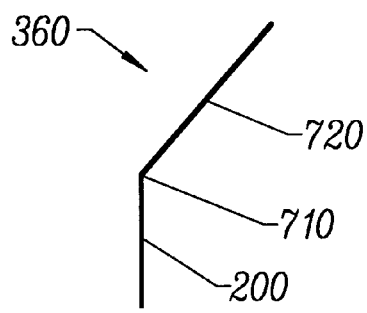

FIGS. 7A, 7B and 7C illustrate another embodiment where the funnel 360, in addition to folding about the top of the reservoir 200, folds about itself when moving between an expanded and unexpanded position. FIG. 7A illustrates a profile of a section of the funnel 360 in an unexpanded position. The funnel 360 is folded inwardly about a point at the top of the reservoir 710 and at a point along the receiving portion 720 of the funnel 360. FIG. 7B illustrates the funnel 360 in a partially expanded position, and FIG. 7C illustrates the funnel 360 in a fully expanded position. This embodiment provides for a larger funnel mouth without requiring a deeper reservoir to store the funnel when it is unexpanded.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A urine specimen collecting system comprising:

a collection reservoir having a top and a bottom;

a funnel having a receiving and connecting portion, said connecting portion coupled with said top of said reservoir for collection of a urine specimen through said funnel into said reservoir; and an extension coupled to said funnel for moving said funnel between an unexpanded and an expanded position;

wherein said receiving portion of said funnel has an area larger than said connecting portion when expanded, and said receiving portion has an area smaller than said connecting portion when unexpanded;

wherein said funnel is substantially contained within said reservoir when unexpanded, and is substantially outside of said reservoir when expanded;

wherein said receiving portion of said funnel is inwardly and outwardly foldable about a point at the top of the reservoir between a first position, wherein the receiving portion is inside of and substantially in contact with the connecting portion, and a second position, wherein the receiving portion is substantially outside of the connecting portion, so that a wide mouth is formed in the second position.

2. A urine specimen collecting system comprising:

a collection reservoir means having a top and a bottom;

a funnel means having a receiving and connecting portion, said connecting portion coupled with said top of said reservoir means for collection of a urine specimen through said funnel means into said reservoir means; and an extension means coupled to said funnel means for moving said funnel means between an unexpanded and an expanded position;

wherein said receiving portion of said funnel means has an area larger than said connecting portion when expanded, and said receiving portion has an area smaller than said connecting portion when unexpanded;

wherein said funnel means is substantially contained within said reservoir means when unexpanded, and is substantially outside of said reservoir means when expanded;

wherein said receiving portion of said funnel is inwardly and outwardly foldable about a point at the top of the reservoir between a first position, wherein the receiving portion is inside of and substantially in contact with the connecting portion, and a second position, wherein the receiving portion is substantially outside of the connecting portion, so that a wide mouth is formed in the second position.

3. A urine specimen collecting system for use with a collection reservoir having a top and a bottom comprising:

a funnel having a receiving and connecting portion, said connecting portion coupled with said top of said reservoir for collection of a urine specimen through said funnel into said reservoir;

wherein said receiving portion of said funnel is inwardly and outwardly foldable about a point at the top of the reservoir between a first position, wherein the receiving portion is inside of and substantially in contact with the connecting portion, and a second position, wherein the receiving portion is substantially outside of the connecting portion, so that a wide mouth is formed in the second position.

4. The system of claim 3, further comprising:
an extension coupled to said funnel for moving said funnel between said unexpanded and expanded position.

5. The system of claim 4, wherein said extensions are two tabs located on opposite ends of a non-specimen receiving surface of said funnel.

6. The system of claim 3, wherein said funnel lies is substantially contained within said reservoir when unexpanded and is substantially outside of said reservoir when expanded.

7. The system of claim 3, wherein said funnel has ridges.

8. The system of claim 7, wherein said ridges lie along the long axis of the funnel.

9. The system of claim 7, wherein said ridges lie circumferentially along the short axis of the funnel.

10. The system of claim 3, wherein the material of the system comprises any of:
metal, plastic, paper, and rubber.

11. The system of claim 3, wherein said receiving portion of said funnel has an area larger than said connecting portion when expanded, and said receiving portion having an area smaller than said receiving portion when unexpanded.

12. The apparatus of claim 3 further comprising:
a liner for sealably connecting said top portion of said collection reservoir to said connecting portion of said funnel.

13. The apparatus of claim 12, wherein said liner is coupled to any of:
said collection reservoir and said funnel.

14. The apparatus of claim 3, wherein a portion of said funnel is foldable inwardly and outwardly about a point on said receiving portion of said funnel when moving between said unexpanded and expanded position.

15. The apparatus of claim 3, wherein an aperture formed by said funnel in said unexpanded position allows a pipet to extract said specimen from said collection reservoir.

16. A method for collecting urine, comprising the steps of:
providing a collection reservoir having a top and a bottom;
providing a funnel having a receiving and connecting portion, said connecting portion coupled with said top of said reservoir for collection of a urine specimen through said funnel into said reservoir; and
moving the funnel between an unexpanded and an expanded position with an extension coupled to said funnel;
wherein said receiving portion of said funnel has an area larger than said connecting portion when expanded, and said receiving portion has an area smaller than said connecting portion when unexpanded;
wherein said funnel is substantially contained within said reservoir when unexpanded, and is substantially outside of said reservoir when expanded;
wherein said receiving portion of said funnel is inwardly and outwardly foldable about a point at the top of the reservoir between a first position, wherein the receiving portion is inside of and substantially in contact with the connecting portion, and a second position, wherein the receiving portion is substantially outside of the connecting portion, so that a wide mouth is formed in the second position.

17. A method for collecting urine, comprising the steps of:
providing a collection reservoir means having a top and a bottom;
providing a funnel means having a receiving and connecting portion, said connecting portion coupled with said top of said reservoir means for collection of a urine specimen through said funnel means into said reservoir means; and
moving the funnel means between an unexpanded and an expanded position with an extension means coupled to said funnel means;
wherein said receiving portion of said funnel means has an area larger than said connecting portion when expanded, and said receiving portion has an area smaller than said connecting portion when unexpanded;
wherein said funnel means is substantially contained within said reservoir means when unexpanded, and is substantially outside of said reservoir means when expanded;
wherein said receiving portion of said funnel is inwardly and outwardly foldable about a point at the top of the reservoir between a first position, wherein the receiving portion is inside of and substantially in contact with the connecting portion, and a second position, wherein the receiving portion is substantially outside of the connecting portion, so that a wide mouth is formed in the second position.

18. A method for collecting a urine specimen with a collection reservoir having a top and a bottom comprising the steps of:
providing a funnel having a receiving and connecting portion, said connecting portion coupled with said top of said reservoir for collection of a urine specimen through said funnel into said reservoir;
wherein said receiving portion of said funnel is inwardly and outwardly foldable about a point at the top of the reservoir between a first position, wherein the receiving portion is inside of and substantially in contact with the connecting portion, and a second position, wherein the receiving portion is substantially outside of the connecting portion, so that a wide mouth is formed in the second position.

19. The method of claim 18, further comprising the step of:
moving said funnel between an unexpanded and expanded position with an extension means coupled to said funnel means.

20. The method of claim 19, wherein said extension means are two tabs located on opposite ends of a non-specimen receiving surface of said funnel.

21. The method of claim 18, wherein said receiving portion of said funnel has an area larger than said connecting portion when expanded, and said receiving portion having an area smaller than said receiving portion when unexpanded.

22. The method of claim 18, wherein said funnel lies is substantially contained within said reservoir when unexpanded and is substantially outside of said reservoir when expanded.

23. The method of claim 18, wherein said funnel has ridges.

24. The method of claim 23, wherein said ridges lie along the long axis of the funnel.

25. The method of claim 23, wherein said ridges lie circumferentially along the short axis of the funnel.

26. The method of claim 18, wherein the material of said reservoir comprises any of:

metal, plastic, paper, and rubber.

27. The method of claim 18, wherein the material of the funnel comprises any of:

metal, plastic, paper and rubber.

28. The method of claim 18 further comprising the step of:

sealably connecting the top portion of the collection reservoir to the connecting portion of said funnel with a liner.

29. The method of claim 28, wherein said liner is coupled to any of:

said collection reservoir and said funnel.

30. The method of claim 18, wherein a portion of said funnel is foldable inwardly and outwardly about a point on said receiving portion of said funnel when moving between said unexpanded and expanded position.

31. The method of claim 18, wherein an aperture formed by said funnel in said unexpanded position allows a pipet to extract said specimen from said collection reservoir.

* * * * *